United States Patent [19]

Cavallotti et al.

[11] Patent Number: 5,703,245

[45] Date of Patent: Dec. 30, 1997

[54] PROCESS FOR REDUCING WATER AND POLAR IMPURITIES IN IMIDO-ALKANPERCARBOXYLIC ACIDS

[75] Inventors: Claudio Cavallotti; Gilberto Nucida; Claudio Troglia, all of Milan, Italy

[73] Assignee: Ausimont, S.p.A., Italy

[21] Appl. No.: 777,697

[22] Filed: Dec. 20, 1996

[30] Foreign Application Priority Data

Dec. 21, 1995 [IT] Italy .................. MI95A2717

[51] Int. Cl.⁶ .................. C07D 209/48

[52] U.S. Cl. .................. 548/473; 548/476; 568/558; 568/561

[58] Field of Search .................. 548/479, 473, 548/476; 568/558, 561; 210/634

[56] References Cited

U.S. PATENT DOCUMENTS

| 5,061,807 | 10/1991 | Gethoffer | 548/473 |
| 5,208,340 | 5/1993 | Cavallotti | 548/479 |
| 5,310,934 | 5/1994 | Cavallotti | 548/479 |
| 5,470,988 | 11/1995 | Jaekel | 548/479 |
| 5,487,818 | 1/1996 | Cavallotti | 203/41 |

FOREIGN PATENT DOCUMENTS

| 0 325 288 B1 | 7/1989 | European Pat. Off. | 548/473 |
| 0 325 289 B1 | 7/1989 | European Pat. Off. | 548/473 |
| 0 349 940 A1 | 1/1990 | European Pat. Off. | 548/473 |
| 0 490 409 A1 | 6/1992 | European Pat. Off. | 548/473 |
| 0 556 769 A1 | 8/1993 | European Pat. Off. | 548/473 |
| 0 560 155 A1 | 9/1993 | European Pat. Off. | 548/473 |
| 0 670 821 A1 | 7/1994 | European Pat. Off. | 548/473 |

Primary Examiner—Ernest G. Therkorn
Attorney, Agent, or Firm—Finnegan, Henderson, Farabow, Garrett & Dunner, L.L.P.

[57] ABSTRACT

Process for reducing the content of water in imido-alkanpercarboxylic acids comprising heating a suspension of imido-alkanpercarboxylc acid in water up to the complete solid melting and subsequent separation of the organic phase from the aqueous phase and recovery of the organic phase containing the imido-alkanpercarboxylic acid.

17 Claims, No Drawings

PROCESS FOR REDUCING WATER AND POLAR IMPURITIES IN IMIDO-ALKANPERCARBOXYLIC ACIDS

The present invention relates to a process for recovering imido-alkanpercarboxylic acids from aqueous slurries, known compounds and utilized as bleaching agents in detergent compositions or as main components of disinfectant or oxidizing compositions. These products combine good bleaching properties with a good storage stability.

The processes for preparing said imido-alkanpercarboxylic acids are well known in the literature and comprise oxidizing in presence of hydrogen peroxide and of a strong acid of the imido-alkancarboxylic acid precursors.

The latter, in the case of the phthalimido-alkancarboxylic acid, is obtained by condensation of phthalic anhydride, or phthalic acid and amino acids or lactams in the presence or in the absence of water, with pressure from 1 to 30 bar, at temperatures ranging from 100° to 250° C. and with reaction times from 5 to 20 hours. See for instance European patents EP 325,289, EP 325,288, EP 349,940. See for instance also European patent 490,409 wherein a process with high yields in percarboxylic acid is described by operating in the presence of particular solvents, for instance $CH_2Cl_2$ and $CHCl_3$. The solution of percarboxylic acid in solvent was then separated from the aqueous phase containing sulphoric acid and hydrogen peroxide.

The solution containing the percarboxylic acid is subjected to a removal process of the solvent for recovering the useful product. See for instance European patent EP 560,155 wherein treatment processes of the solution with water are described which lead to obtain percarboxylic acid (PAP) in humid crystalline powder (cake) by filtering or by centrifugation of impure aqueous slurries for organic solvents, for instance $CH_2Cl_2$ or ethyl acetate, with residual content of water in the range of 20% by weight and of the residual solvent from 50 to 2500 ppm.

Generally since the levels of chloro-containing solvents allowed in the formulations of alkanpercarboxylic acids are very low, a successive purification treatment is further carried out with another non chlorinated solvent, for instance ethylacetate. See for instance European patent EP 556,769.

In this way, however, the alkanpercarboxylic acid contained measurable amounts of another solvent, such as ethylacetate.

After all these treatments the amount of water present in the alkanpercarboxylic acid is always in the range of 20% by weight or higher percentages.

For preparing formulations of alkanpercarboxylic acids this amount of water is too high wherefore it must be reduced by means of drying processes which are very slow in order to avoid explosions, very frequent when one operates with peroxidic ompounds.

This is a critical step of the industrial processes both owing to its dangerousness and its low productivity.

Besides, with these processes one should reach a constant value of said reduced content of water for the requirements of the forward manufacturing processes on the solid.

It was felt the need to have available an industrial process allowing to obtain alkanpercarboxylic acids with the reduced content in water around 10% by weight, and constant for the successive formulations by avoiding the drying process, very slow and dangerous from the industrial point of view.

Object of the present invention is a process for reducing the content of water in imido-alkanpercarboxylic acids having a content in water higher than 12% by weight, which comprises heating a suspension of imido-alkanpercarboxylc acid in water up to the complete solid melting and subsequent separation of the organic phase from the aqueous phase and recovery of the organic phase containing the imido-alkanpercarboxylic acid.

More particularly an object of the present invention is a process for reducing water as described above wherein the imido-alkanpercarboxylic acid is the phthalimido-peroxyhexanoic acid.

The imido-alkanpercarboxylic acids which can be treated according to the process of the invention have the general formula:

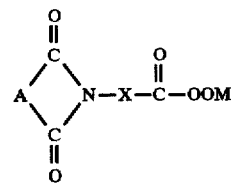

wherein A and X have the meaning as defined hereunder and are obtained according to known peroxidation processes in the presence of hydrogen peroxide and of a strong acid generally at temperatures from 5° to 50° C. of an imido-alkancarboxylic acid precursor otainable by reaction of
A) a1) an anhydride of formula

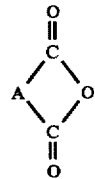

or the corresponding acids,
with
b1) an aminoacid of formula $$H_2N-X-C-OH$$
with an O double-bonded to C with
c1) water;
or a1) with
b2) a lactam of general formula

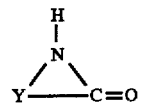

with
c1) water;
at temperatures comprised betweeen 100° C. and 250° C., under pressure of an inert gas from 1 to 30 bar, for reaction times from 2 to 20 hours;
wherein A indicates a group of formula

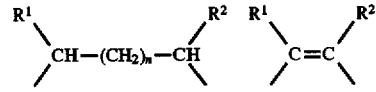

-continued or

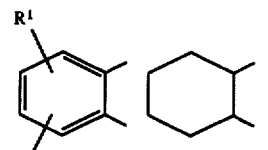

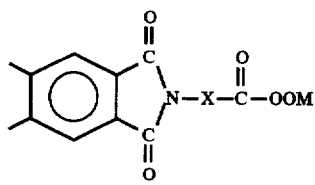

n is an integer 0, 1 or 2, $R^1$ is hydrogen, chlorine, bromine, alkyl $C_1$–$C_{20}$, alkenyl $C_2$–$C_{20}$, aryl or alkylaryl, $R^2$ is hydrogen, chlorine, bromine or a group of formula —$SO_3M$, —$CO_2M$, —$CO_3M$, —$OSO_3M$, M indicates hydrogen, an alkaline metal or ammonium ion or the equivalent of an alkaline-earth metal ion and X indicates alkylene $C_1$–$C_{19}$ or arylene;

Y is =X and preferably an alkylene $C_3$–$C_{19}$;

The ratio by moles generally between a1/(b1 or b2)/c1 is comprised between 1/0.8:1.2/0.5–3. Preferably the ratio by moles a1/(b1 or b2)/c1 is comprised between 1/1.01:1.1/0.5:2.5, more preferably between 1/1.05:1.1/1–2.

The preferred compounds of type b) are those of class b2).

Among the compounds of class a1) the following anhydrides or the corresponding acids can be mentioned: succinic, glutaric, maleic, trimellitic, phthalic, pyromellitic and alkyl- or alkenyl-succinic anhydride. Phthalic anhydride or pthalic acid are preferably used.

Among the compounds of class b1) it can be mentioned: omega-aminobutyric acid, omega-aminovalerianic-, omega-aminocaproic and omega-aminolauric acid.

Among the compounds of class b2) can be mentioned as the preferred ones: gamma-pyrrolidone, delta-piperidone, epsilon-caprolactam and omega-laurolactam, epsilon-caprolatam (CPL) is particularly preferred.

Preferably in phase A) the temperature is comprised between 130° C. and 180° C. and the pressure between 4 and 8 bar.

Preferably phase A) is carried out in the presence of a solvent, preferably $CH_2Cl_2$ and $CHCl_3$, more preferably $CH_2Cl_2$.

These last solvents, indeed, as described in EP patent 490,409, are the most suitable to carry out the subsequent peroxidation operation.

Among imido-alkanpercarboxylic acids can be mentioned phthalimido-peracetic acid, phthalimido peroxyhexanoic acid, 3-phnhalimido-perpropionic acid, 4-phthalimido-perbutyric acid, 2-phthalimido-diperglutaric acid, 2-phthalimido-dipersuccinic acid, 3-phthalimido-perbutyric acid, 2-phthalimido-perpropionic acid, 3-phthalimido-diperadipic acid, naphthalimido-peracetic acid, 2-phthalimido-monopersuccinic acid.

Without being tied to any theory, according to the Applicant, the present invention is based on the fact that pure imido-alkanpercarboxylic acids, obtained for instance by crystallization from organic solutions, have a melting point very near to the decomposition temperature; while surprisingly imido-percar-boxylic acids in the presence of water are capable of melting at a lower temperature, very far from the melting temperature, by forming eutectics. Moreover said eutectics are pratically unsoluble in the aqueous phase and have a viscosity and a density such as to be easily separable from the water itself.

The present invention is illustrated in detail as an example for the pthhalimido-peroxyhexanoic acid. For instance in the case of the pthalimido-peroxyhexanoic acid the temperature of formation of the eutectic with water is of about 72° C., while the decomposition temperature of the pure acid is about 92° C. The eutectic has a density at 75° C. of 1.229 g/ml, the viscosity at 75° C. is 15 cPoise.

This fact is completely unexpected and allows an easy separation of the eutectic from the aqueous phase for instance by simple decantation in a phases separator.

Even more surprising is the fact to have found that the amount of water in the eutectic composition is of about 11.5% by weight, which is the amount of water industrially useful for preparing various formulations based on said solid percarboxylic acids.

The observation of such surprising phenomenon has led to the following remarks:

the amount of water which is bound to the phthalimidoperoxyhexanoic acid (PAP) at 72°–73° C. to form the above mentioned eutectic is constant, independently from the amount of water utilized to perform its formation, and is of about 2 moles per mole of peroxyacid, corresponding to about 11.5% by weight. Moreover it has been noticed that the content in water can be further reduced if the eutectic is solidified, for instance as defined hereinafter on a flaking-belt.

The amount of peracid which accumulates in the aqueous phase overlying the eutectic is very low.

The stability of the phthtalimido-peroxyhexanoic acid to the eutectic composition is high, by operating at temperatures even comprised between 72° and 90° C., preferably between 75° and 80° C.

Moreover it has been unexpectedly found that the stability of the peracid to the eutectic composition between 72° and 90° C. can be further improved if during the melting also sequestering substances, also in very low amounts, generally in the range from 100 to 10000 ppm, are used. Hydroxycarboxylic acids for instance can be mentioned, among them it cam be cited citric acid; amino-polycarboxylic acids, of which ethylendiaminotetramethylphosphonic acid (EDTMP) can be mentioned; pyridincarboxylix acids, of which the dipicolinic acid can be cited; or polyphosphonic acids, of which 1-hydroxy-ethyliden-1,1-diphosphonic acid, indicated for the sake of brevity as HEDP, can be mentioned.

As said above from the eutectic it is possile to easily obtain a solid product of the imido-alkanpercarboxylic acid, by solidification of the eutectic at temperatures lower than 72° C., for instance by pouring the melt on the cooled flaking belt. In this way one already obtains a peracid product not in powder, therefore with all the advantages not to have to granulate the product to make the successive operations easier during the formulation and/or the transport. In this way a product in the form of wet flakes is obtained with a content in water practically constant, generally 8–10% by weight, therefore even lower than the amount of water of the eutectic composition.

The constancy of the water content in the final peracid is a very important factor for the purpose of the successive treatments of the product finishing.

The above mentioned formation of the eutectic has also the further effect to purify the imidoalkanpercarboxylic acid from possible polar substances present in the product such as impurities, such as for instance, the reactants utilized in the preparation of the precursor of the carboxylic acid, the acid precursor and especially from traces of the solvents utilized for the peroxydic synthesis or in purification treatments of the art described above and undesirable in the finished product.

To this end another method of solidification can be mentioned which consists in obtaining the peracid in the form of irregular granules by introducing the melted eutectic in a mass of cool water, for instance at 15° C., strongly stirred.

In this case it is not obtained a constance of the humidity percentage of the product mass, isolable by filtering or centrifugation from the new slurry obtained, but only an effect of purification of the peracid from the polar impurities, such as those deriving from the solvents indicated above.

A further object of the present invention resides in that by the process of the present invention it is possible to directly submit to purification the peracid/water slurry obtainable directly by peroxidation synthesis after separation of the solvent, for instance the chloro-containing solvents of patent EP 490,409, without washings with other solvents to remove the cloro-containing solvents, as said above, for instance by treatment with ethylacetate, by stripping treatment of the melted eutectic with vapour at reduced pressure.

For instance stripping can be made with steam on the eutectic melted at temperatures of 72°–75° C. and under vacuum, for instance about 280–300 mmHg.

This further object of the invention is quite unexpected since one could expect that the peracid in the presence of vapour at stripping temperatures could suffer decompositions.

Such methodology is utilizable in continuous industrial processes and allows to reutilize the melting aqueous phase in equilibrium with the eutectic for obtaining new slurries of raw product deriving from the peroxidation to direct to the melting process to eutectic and to the successive stripping of the eutectic for the further purification from the impurities mentioned. In this way the small losses of peracid accumulated in the aqueous phase as said above, are avoided.

In this way the peracid purified by the stripping method results free from solvents, for instance chloro-containing solvents, which are lower than the analytical limits, determined by gas chromatography.

The stripping, preferably in counter-current, with vapour at reduced pressure is carried out for instance in a jacketed column, for instance filled with Rashig rings and the vapour, in countercurrent to the eutectic to be purified, enters from the bottom of the column at a temperature of 72°–75° C. and by maintaining a vacuum in the column, generally comprised between 280–300 mmHg. The peracid/H$_2$O eutectic in the melted state is fed from the column head, preferably with a flow-rate lower than that of the vapour, the ratio by weight eutectic/vapour is generally comprised between 2:1 and 1:2.

The following examples are given for illustrative purposes but are not limitative of the scope of the present invention.

EXAMPLES 1-2-3-4-5-6-7

50 g of phthalimido-peroxyhexanoic acid (PAP) having a purity of 98.1% by weight are introduced in a 500 ml cylindrical glass reactor, jacketed and endowed with outlet on the bottom, together with 244 g of demineralized water.

Under continuous stirring, this slurry is heated to 75° C., temperature at which the peracid melting is completed with formation of an eutectic immiscible in the aqueous medium and having a density of 1.229 g/ml.

After the residence times reported in table 1, stirring is stopped and after 5 minutes of decantation, small amounts of the melt separated from the aqueous medium are taken through the bottom outlet, which are immediately diluted with suitable amounts of solvent, such as acetonitrile or dioxane, compatible with the chosen analytical methodology (HPLC) for determining the content in PAP.

The tests are repeated by utilizing water in the same amount, but containing the stabilizers indicated in Table 1.

From Table 1 it is possible to notice how small amounts of stabilizers inhibit even more the degradation of the PAP contained in the eutectic at the temperature of 75° C., when one operates for times from 1 hour to 3 hours.

One has indeed 42% of loss of active oxygen after 1 hour of residence at 75° C. of the eutectic formed starting from demineralized water as such, with respect to 1.0–2.6% by weight of similar loss noticed for the eutectic obtained by employing water added with sequestering agents, operating with residence times of 1 hour.

Also with residence times of 3 hours the losses in content of peroxydic oxygen of the peracid range between 2.5 and 5.6% with respect to a loss of 72% obtained by operating only with water.

EXAMPLES 8-9-10

By proceeding as described in examples 1-7 melting tests of the PAP having a title of 98.1% by weight are here carried out at 75° C., 85° C. and 90° C. in an aqueous medium containing 500 ppm of HEDP and noticing, after 30 minutes of residence of the PAP/H$_2$O eutectic at said temperatures, the degradation suffered by the peracid, as loss of active oxygen. The data are reported in Table 2.

As it is possible to notice from Table 2, also by carrying out meltings of the PAP in H$_2$O at rising temperatures from 75° C. to 90° C., degradations which can be considered moderate from the point of view of the industrial safety, are noticed.

EXAMPLES 11-12-13-14

According to the operating modalities of examples 1-7, aqueous slurries added with 500 ppm of HEDP, containing different concentrations of solid and having different purity, and in remarkable amounts from 0.5 to 5 Kg, are brought to melting, at the temperature of 75° C., in 10 l jacketed glass reactors, by noticing after 30 minutes of decantation the content of H$_2$O in the formed eutectic, determined by Karl Fischer analysis and in the obtained flakes by pouring the melted eutectic on a flaking-belt having a belt length of 4 m and a belt width of 30 cm.

As it is possible to verify from Table 3, the content of H$_2$O in the eutectic at 75° C. is constant, about 11% by weight.

Also the residual humidity in the PAP flakes, of a thichness variable from 1-2 mm, obtained by cooling of the melt on the flaking-belt is about constant, around 9% by weight, and lower than the content of water of the eutectic.

EXAMPLES 15-16-17-18-19

According to the methodology described in examples 11-14, aqueous slurries having a different content of solid are prepared, by employing PAP with variable purity, impure for CH$_2$Cl$_2$ or ethyl acetate (ET. AC.).

By bringing these slurries to melting in the presence of 500 ppm of HEDP and by then operating in such a way as to arrive to obtain flakes as indicated in the examples of Table 3, or granules of wet PAP obtained by melt casting in stirred cool water at 15° C., a high reduction of the above mentioned impurities, variable from 30% to 68%, was noticed in the final product.

EXAMPLE 20

2.31 g of solid PAP, having a title of 97.2% and containing 2000 ppm of $CH_2Cl_2$, together with 469 g of demineralized $H_2O$ containing 500 ppm of Sequion® 10H, are introduced in the melter/separator container located in the head of the stripping column.

Under continuous stirring the temperature of the slurry is brought to 75° C., then, when the solid is melted, stirring is stopped, and, after 5 minutes of stay, it is dosed in about 1 hour the eutectic formed in the stripping column in vapour countercurrent at 75° C. and 288 mmHg of absolute vacuum with a vapour flow-rate of 350 g/hour and a melt flow-rate of 250 g/hour.

The product flowing out from the stripping is continuously discharged, in the melted state, from the bottom of the column in 1 liter of cool water having temperature of 15° C. and maintained under stirring.

228 g of PAP in granules having 97.5% of purity, containing 5 ppm of residual $CH_2Cl_2$ are obtained by filtering the slurry and drying of the solid granules in an air-ventilated stove, at temperature of 40° C.

The content of $CH_2Cl_2$ is determined by gaschromatographic analysis.

EXAMPLE 21

An amount of 236 g of crystalline solid PAP, with title of 95.2% and containing 0.2% of $CH_2Cl_2$ is broungt to melting, at 75° C., in an aqueous medium added with 500 ppm of Sequion® 10H (sequestering agents). After separation in the decanter/batcher, 254 g of eutectic are obtained, containing about 1600 ppm of $CH_2Cl_2$.

The melted eutectic is fed in 1 hour to the stripping column, obtaining at the end 264 g of wet flakes, the humidity being of about 8% by weight, of purified PAP, the thickness of the flakes being of 1.4 mm, containing 8 ppm of residual $CH_2Cl_2$, and 89.24% of phthalimido-peroxyhexanoic acid.

EXAMPLE 22

An amount of 400 g of the melting water coming from the test described in example 21 is utilized to melt 200 g of PAP having a title of 97.2%, impure of 2000 ppm of $CH_2Cl_2$.

The formed $PAP/H_2O$ eutectic is treated in the stripping column in vapour counter-current with a flow-rate of 350 g/hour at 288 mmHg of absolute vacuum, by obtaining 208 g of wet flakes which, after drying in a ventilated stove at 40° C. for 2 hours, show a content of phthalimido-peroxyhexanoic acid of 96.8% and having a content of $CH_2Cl_2$ of 10 ppm.

EXAMPLE 23

A slurry formed by 10 l of demineralized water added with 1000 ppm of Sequion® 10H and 3% of a crystalline solid product to be purified, containing 97.5% of phthalimido-peroxyhexanoic acid and 890 ppm of $CH_2Cl_2$, is continuously fed, under stirring and at the temperature of 40° C. and with a flow-rate of 8–10 l/h, through a coil exchanger wherein at 75° C. the PAP passes to the melted state and the formed eutectic is gathered in the batcher/separator located at the head of the stripping column.

The aqueous phase separated in the separator is sent by continuous outlet in the starting slurry, where 250 g/hour of PAP to be purified are always continuously added.

Always continously, the melted $PAP/H_2O$ eutectic is batched (dosed) to the stripping column with a flow-rate of 250 ml/h and with vapour in countercurrent at the flow-rate of 350 g/hour. After 4 hours, about 940 g of wet flakes are obtained, the humidity being 8% by weight and containing on average 88.8% of phthalimido-peroxyhexanoic acid and 12 ppm of $CH_2Cl_2$.

TABLE 1

Stability of the peracid $(PAP)/H_2O$ eutectic at 75° C. in an aqueous medium in the absence and in the presence of stabilizers

| EXAMPLE No. | PAP 98.1% by wt. used (g) | AQUEOUS MEDIUM | | | % PEROXIDIC LOSS OF THE PAP CONTAINED IN THE PAP/H₂O EUTECTIC | | |
|---|---|---|---|---|---|---|---|
| | | g | STABILIZER TYPE | CONCENTRATION % by weight | AFTER 5' | AFTER 1 hour | AFTER 3 hours |
| 1 | 50 | 244 | — | — | 1.6 | 42 | 72 |
| 2 | " | " | CITRIC ACID | 1 | — | 2.08 | 5.1 |
| 3 | " | " | HEDP | 0.05 | — | 1.05 | 2.6 |
| 4 | " | " | HDDP | 0.025 | — | 0.97 | 2.5 |
| 5 | " | " | ATMP | 0.05 | — | 1.28 | 3.06 |
| 6 | " | " | EDTMP | 0.05 | — | 2.58 | 5.43 |
| 7 | " | " | DIPICOLINIC ACID | 0.01 | — | 2.09 | 5.6 |

HEDP = $CH_3 COH (H_2PO_3)_2$
HDDP = $CH_3 (CH_2)_{11} COH(H_2PO_3)_2$
ATMP = $N(CH_2PO_3H_2)_3$
EDTMP = $(H_2PO_3CH_2)_2NC_2H_4N(CH_2PO_3H_2)_2$

TABLE 2

Stability of the peracid (PAP)/H₂O eutectic at 75°–90° C. in an aqueous medium added with stabilizers

| EXAMPLE No. | PAP 98.1% by wt. used (g) | AQUEOUS MEDIUM g | STABILIZER TYPE | % weight | STAY IN THE AQUEOUS MEDIUM | % PEROXY LOSS OF THE PAP CONTAINED IN THE EUTECTIC PAP STAY IN THE THE TEMPERATURe °C. | % LOSS weight |
|---|---|---|---|---|---|---|---|
| 8 | 50 | 244 | HEDP | 0.05 | 30' | 75 | 0.6 |
| 9 | " | " | " | " | " | 85 | 2.1 |
| 10 | " | " | " | " | " | 90 | 3.4 |

TABLE 3

Content of water in the PAP/H₂O Eutectic obtained by melting aqueous slurries at different PAP concentrations and in the isolated product in flakes

| EXAMPLE NO. | PAP AQUEOUS SLURRIES PAP (% BY WT.) | PAP PURITY (% BY WT.) | MELTING TEMPERATURE (°C.) | WATER IN THE EUTECTIC (% BY WEIGHT) | WATER IN THE FLAKES (% BY WEIGHT) |
|---|---|---|---|---|---|
| 11 | 5 | 98.1 | 75 | 11.24 | 8.7 |
| 12 | 17 | 96.4 | " | 11.34 | 9.4 |
| 13 | 17 | 94.7 | " | 11.36 | 9.1 |
| 14 | 33 | 94.7 | " | 11.42 | 8.9 |

TABLE 4

Purification of the PAP in flakes or granules, coming from the melting process of aqueous slurries at different concentrations

SLURRY MELTING AT 75° C. AND SOLIDIFICATION BUTECTIC

| EXAMPLE No. | EMPLOYED PUP COMPOSITION IN THE SLURRY PAP (% by wt) | $CH_2Cl_2$ (ppm) | ET.AC. (ppm) | SLURRY SOLID CONC. (% BY WEIGHT) | FLAKES REFERRED TO ANHYDROUS SOLID PAP (% by wt) | $CH_2Cl_2$ (ppm) | ET.AC (ppm) | GRANULES REFERRED TO ANHYDROUS SOLID PAP (% by wt) | $CH_2Cl_2$ (ppm) | ET.AC (ppm) |
|---|---|---|---|---|---|---|---|---|---|---|
| 15 | 98.1 | 66 | — | 5 | 98.7 | 23 | — | 98.8 | 24 | — |
| 16 | 96.1 | — | 100 | 5 | 97.7 | — | 5 | | | |
| 17 | 96.4 | 150 | — | 5 | 97.8 | 48 | — | | | |
| 18 | 96.4 | 150 | — | 17 | 97.8 | 68 | — | 97.7 | 70 | — |
| 19 | 94.7 | 250 | — | 33 | 96.1 | 165 | — | | | |

We claim:

1. Process for reducing the content of water in imido-alkanpercarboxylic acids having a content in water higher than 12% by weight, which comprises heating a suspension of imido-alkanpercarboxylc acid in water up to the complete solid melting and subsequent separation of an organic phase from an aqueous phase and recovery of the organic phase containing the imido-alkanpercarboxylic acid.

2. Process for reducing the content of water in imido-alkanpercarboxylic acids according to claim 1, wherein the imido-alkanpercarboxylic acids have the general formula:

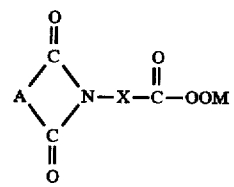

wherein A indicates a group of formula

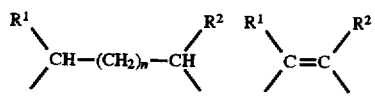

or

-continued

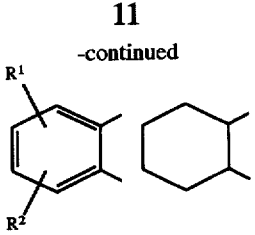

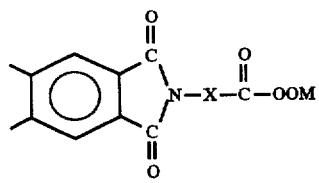

n is an integer 0, 1 or 2, $R^1$ is hydrogen, chlorine, bromine, alkyl $C_1-C_{20}$, alkenyl $C_2-C_{20}$, aryl or alkylaryl, $R^2$ is hydrogen, chlorine, bromine or a group of formula $-SO_3M$, $-CO_2M$, $-CO_3M$, $-OSO_3M$, M indicates hydrogen, an alkaline metal or ammonium ion or the equivalent of an alkaline-earth metal ion and X indicates alkylene $C_1-C_{19}$ or arylene;

Y is $=X$.

3. Process for reducing the content of water in imido-alkanepercarboxylic acids according to claim 2, wherein Y is an alkylene $C_3-C_{19}$.

4. Process for reducing the content of water in imido-alkanpercarboxylic acids according to claim 1, wherein the acid is the phthalimido-peroxyhexanoic acid.

5. Process for reducing the content of water in imido-alkanpercarboxylic acids according to claim 4, wherein the acid is phthalimido-peroxyhexanoic acid and the melting temperature of the eutectic is about 72° C.

6. Process for reducing the content of water in imido-alkanpercarboxylic acids according to claim 1, wherein the imido-alkanpercarboxylic acids are obtainable by peroxidation processes in the presence of hydrogen peroxide and of a strong acid of an imido-alkancarboxylic acid precursor obtainable by reaction of A) a1) an anhydride of formula

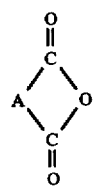

or the corresponding acids,
with
b1) an aminoacid of formula

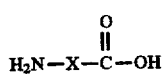

with
c1) water;
or a1) with b2) a lactam of general formula

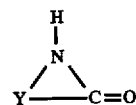

with
c1) water;
at temperatures comprised betweeen 100° C. and 250° C., under pressure of an inert gas from 1 to 30 bar, for reaction times from 2 to 20 hours; the meaning of the symbols being the one indicated above.

7. Process for reducing the content of water in imido-alkanpercarboxylic acids according to claim 6, wherein the imido-alkanpercarboxylic acids are phthalimido-peracetic acid, 3-phthalimido-perpropionic acid, 4-phthalimido-perbutyric acid, 2-phthalimido-diperglutaric acid, 2-phthalimido-dipersuccinic acid, 3-phthalimido-perbutyric acid, 2-phthalimido-perpropionic acid, 3-phthalimido-diperadipic acid, naphthalimido-peracetic acid, 2-phthalimido-monopersuccinic acid.

8. Process for reducing the content of water in imido-alkanpercarboxylic acids according to claim 6, wherein the peroxidation reaction is carried out in solvent.

9. Process for reducing the content of water in imido-alkanpercarboxylic acids according to claim 8, wherein the solvent is chosen between $CH_2Cl_2$ and $CHCl_3$.

10. Process for reducing the content of water in imido-alkanpercarboxylic acids according to claim 1, wherein sequestering agents are added.

11. Process for reducing the content of water in imido-alkanpercarboxylic acids according to claim 10, wherein the sequestering agents are selected from hydroxycarboxylic acids, amino-polycarboxylic acids, pyridin-carboxylic acids, polyphosphonic acids.

12. Process for reducing the content of water in imido-alkanpercarboxylic acids according to claim 1, wherein the organic phase of the melt is solidified on a cooled belt.

13. Process for reducing the content of water in imido-alkanpercarboxylic acids according to claim 1, wherein the melted organic phase is submitted to a stripping treatment with reduced pressure vapour.

14. Process for reducing the content of water in imido-alkanpercarboxylic acids according to claim 13, wherein the vapour is passed in counter-current.

15. Process for the purification of imido-alkanpercarboxylic acids from polar impurities according to claim 1, comprising heating of a suspension of imido-alkanpercarboxylic acid in water up to the complete melting of the solid, and subsequent separation of the organic phase from the aqueous phase and recovery of the organic phase containing the imido-alkanpercarboxylic acid.

16. Process for the purification of imido-alkanpercarboxylic acids from polar impurities comprising heating of a suspension of imido-alkanpercarboxylic acid in water up to the complete melting of the solid, and subsequent separation of an organic phase from an aqueous phase and recovery of the organic phase containing the imido-alkanpercarboxylic acid.

17. Process for the purification of imido-alkanpercarboxylic acids from polar impurities according to claim 16, wherein the organic phase of the melt is solidified in a mass of cool water.

* * * * *